(12) United States Patent
Kluger et al.

(10) Patent No.: US 6,710,220 B2
(45) Date of Patent: Mar. 23, 2004

(54) PH REDUCING FORMULATION AND DELIVERY SYSTEM FOR A TAMPON

(75) Inventors: Ram Kluger, Pardessea (IL); Simon Benita, Mevasseret Zion (IL); Theodor Stern, Jerusalem (IL)

(73) Assignee: Hi-Gienic Ltd. (IL)

( * ) Notice: Subject to any disclaimer, the term of this patent is extended or adjusted under 35 U.S.C. 154(b) by 55 days.

(21) Appl. No.: 09/856,000

(22) Filed: May 15, 2001

(65) Prior Publication Data

US 2002/0045873 A1 Apr. 18, 2002

(30) Foreign Application Priority Data

Aug. 31, 2000 (IL) .................................................. 138183

(51) Int. Cl.[7] ............................ A61F 13/15; A61F 13/20
(52) U.S. Cl. ...................... 604/360; 604/285; 604/358; 604/379; 604/904
(58) Field of Search ................................. 604/285, 358, 604/360, 379, 904

(56) References Cited

U.S. PATENT DOCUMENTS

| | | | | |
|---|---|---|---|---|
| 4,431,427 A | * | 2/1984 | Lefren et al. | 604/285 |
| 4,661,101 A | | 4/1987 | Sustmann | 604/360 |
| 4,685,909 A | | 8/1987 | Berg et al. | 604/360 |
| 4,816,257 A | * | 3/1989 | Buster et al. | 424/430 |
| 5,116,619 A | * | 5/1992 | Greco et al. | 424/433 |
| 5,618,554 A | * | 4/1997 | Syverson | 424/431 |
| 5,685,872 A | * | 11/1997 | Syverson | 604/360 |
| 6,020,453 A | | 2/2000 | Larsson et al. | 528/272 |
| 6,197,299 B1 | * | 3/2001 | Dohlsten et al. | 424/183.1 |
| 2002/0082571 A1 | * | 6/2002 | Krivan et al. | 604/358 |
| 2002/0102271 A1 | * | 8/2002 | Balaban et al. | 424/190.1 |

FOREIGN PATENT DOCUMENTS

| | | | |
|---|---|---|---|
| JP | 11323113 | 5/1998 | ............. C08J/5/18 |
| WO | wo 91/08726 | 6/1991 | ........... A61F/13/15 |
| WO | WO 99/45976 | 9/1999 | ........... A61L/15/46 |

* cited by examiner

*Primary Examiner*—William Doerrler
*Assistant Examiner*—Mark Shulman
(74) *Attorney, Agent, or Firm*—Ivor R. Elrifi; Barry J. Marenberg; Mintz, Levin, Cohn, Ferris, Glovsky and Popeo, P.C.

(57) ABSTRACT

A formulation effective in reducing the pH in a menstruating vagina or in a tampon inserted therein to below pH 5.5, comprising (a) 3–80% by weight of a solid organic acid polymer; (b) 92–15% by weight of a solid organic acid, and (c) 5–30% of a wetting agent. Also disclosed is a delivery system for releasing an active agent comprising: (a) a deposition comprising the active agent; and (b) a polymeric support on which the deposition is deposited. The delivery system is especially useful in a catamenial tampon for insertion in a human vagina which comprises (a) an inner core comprising an absorbent material; (b) an outer layer comprising a liquid permeable material; and (c) the delivery system.

23 Claims, 13 Drawing Sheets

PH REDUCING FORMULATION AND DELIVERY SYSTEM FOR A TAMPON

FIELD OF THE INVENTION

This invention relates to a pH-reducing formulation, an active agent delivery system and a tampon comprising the same.

BACKGROUND OF THE INVENTION

The normal, healthy human vagina is weakly acidic and has a pH of approximately 4.5. This acid condition of the vagina provides an effective barrier against the growth of pathogenic microorganisms normally associated with vaginal infection, because such microorganisms do not grow below a pH of about 5. If, however, the pH of the vagina becomes less acidic, i.e., higher than about 5, pathogenic microorganisms tend to multiply.

A change in pH of the vagina from the normal of about 4.5 to 5 to a more alkaline pH may be brought about by various vaginal conditions and may occur at any time during the menstrual cycle. During menstruation, in particular, the vagina becomes less acidic due to the presence of menstrual fluid which has a pH of from is about 7 to 8. As a result, the protective barrier provided by the normal acidic condition of the vagina becomes less effective, thereby providing an environment favorable to the growth of the pathogenic microorganisms.

To overcome the reduction in acidity of the vagina and to reestablish the desired normal acidic condition, different formulations and techniques have been developed. Such efforts have included the development of formulations such as solutions, jellies, powders, suppositories, and the like containing acidifying materials which are introduced into the vagina in their prepared form.

While the above-mentioned types of products have met with acceptance, they are subject to numerous disadvantages. The solutions, jellies, powders, and suppositories containing acidifying materials may be inconvenient to handle and apply and are not fully retained in the vagina and tend to escape. In addition, they do not have capacity for absorbing vaginal fluid which may be present in the vagina, particularly during menstruation. Therefore, to use such products during menstruation, it is also necessary to use at the same time a catamenial tampon or similar article.

Other attempts to lower the pH have included physically incorporating acidifying materials into absorbent products by coating, spraying, impregnating and the like, to impart to such products acidifying properties.

U.S. Pat. No. 4,431,427 to Lefren et al, discloses a tampon having incorporated therein one or more organic acids in combination with at least one of oligomer and polymer derivatives of the acids. The acids may be citric, gylcolic, malic, tartaric or lactic acid. The tampon is intended for maintaining a pH of about 4.5 to 2.5 in the fluids absorbed by the tampon during use, thereby inhibiting the growth of pathogenic bacteria in the tampon.

U.S. Pat. No. 4,661,101 to Sustmann discloses a catamenial tampon comprising a microbistatic fibrous absorbant core and an outer covering layer of a pH-regulating fibrous, cell lose material. The cellulose fibers are modified by carboxymethyl groups which are converted into their free acid form by treatment with an acid.

WO 91/08726 discloses a disposable sanitary napkin comprising a water permeable topsheet, an absorbent core and a water impermeable backsheet. The topsheet and/or backsheet comprise absorbable, hydrolyzable and biodegradable substances such as a lactic acid-based or glycolic acid-based polyester. This enhances the disposability of the napkin.

U.S. Pat. No. 6,020,453 to Larsson et al, discloses an absorbent article having a surface material, wherein the surface material includes a surface layer (being the outermost layer) which comprises a lactic acid-based polyester. The surface material is capable of excreting lactic acid to the surrounding urogenital region of menstruating women so as to establish a pH value of at most 4.0. The polyester has a molecular weight of at most 50,000 and the monomer/oligomer concentration is 5–30% by weight.

SUMMARY OF THE INVENTION

It is an object of the present invention to provide a novel formulation capable of reducing the pH in the menstruating vagina and/or in the tampon.

It is a further object of the invention to provide a novel delivery system for use with a feminine hygienic product, such as a tampon, to deliver an active agent to the female urogenital tract.

In a first aspect, the present invention provides a formulation effective in reducing the pH in a menstruating vagina or in a tampon inserted therein to below pH 5.5 comprising:

(a) 3–80% by weight of a solid organic acid polymer;
(b) 92–15% by weight of a solid organic acid; and
(c) 5–30% of a wetting agent.

The formulation of the invention is believed to be effective in reducing the pH to below pH 5.5 in a vagina during menstration and/or in a tampon inserted therein, and more preferably below pH 5.0, within a reasonable amount of time, such as within 0.5 hour. The components of the formulation are:

(a) an organic acid polymer which contributes to the long-term pH reduction;
(b) a solid organic acid which contributes to the immediate pH reduction; and
(c) a wetting agent for facilitating release of the organic acids.

The organic acid polymer of the formulation includes two or more monomers and is primarily non-acidic prior to hydrolysis. Examples of organic acid polymers include polylactic acid, polyglycolic acid and polymalic acid or copolymers of the above. A preferred organic acid polymer in the formulation of the invention is a polymer of lactic acid. Preferred polymers are L-lactide or DL-lactide (LD), a racemic mixture of a cyclic dimer of lactic acid, and polylactic acid (PLA) in the general range of 200–2000 MW. The organic acid polymer comprises 3–80% of the formulation, preferably 60–80%, most preferably 70–80%.

Examples of solid organic acids are citric, malic, maleic, fumaric, succinic, tartaric and oxalic acids. A preferred organic acid is citric acid. The organic acid comprises 92–15% of the formulation, and preferably 30–15%.

Examples of wetting agents which may be used in the formulation of the invention include glycerol, polyethylene glycol (PEG), polypropylene glycol (PPG) and surfactants with an HLB ranging from 10 to 18. Preferred wetting agents are glycerol and PEG-8000. The wetting agent comprises 5–30% of the formulation, and preferably 5–10%.

The formulation may comprise additional substances such as stabilizers, perfuming agents, preservatives, antioxidants, chelating agents, adsorbents, analgesic agents, anti-inflammatory agents, etc.

In a second aspect, the invention provides a delivery system for releasing an active agent it comprising:

(a) a deposition comprising the active agent; and
(b) a polymeric support on which the deposition is deposited.

The active agent may be any agent which performs a necessary function in the vagina such as an anti-bacterial, a pH-reducing or an deodorizing agent. Preferably, the active agent is a pH reducing formulation according to the invention, except that in this aspect of the invention, the wetting agent is optional.

The deposited formulation may include any polymer capable of producing and facilitating a coherent deposition on the polymeric support material. Such polymers include but are not limited to polyesters, olefins, cellulose and cellulose derivatives, PVA and PVP.

The polymeric support may be any polymeric material capable of serving as a support for the deposited material, and includes non-woven as well as woven materials. Examples of such support material include polypropylene, polyethylene, cellulose and cellulose derivatives or any other polymer which can be processed as a fiber.

A preferred shape of the polymeric support is a rectangular strip, which preferably consists of one or more layers, for example, 2–16 layers. Other shapes for the strip are also contemplated as part of the invention.

The delivery system of the invention is preferably used together with a catamenial tampon, as will be explained in more detail below.

Preferably, more than one delivery system will be placed in a tampon on different sides, so as to release the active agent in all directions.

Among the advantages of using the delivery system of the invention for releasing an active agent to the surrounding environment of the female urogenital tract is the contribution both to the economy of the manufacturing process of the tampon as well as to its reproducibility.

In a third aspect of the invention, there is provided A catamenial tampon for insertion in a human vagina comprising:

(a) an inner core comprising an absorbent material;
(b) an outer layer comprising a liquid permeable material; and
(c) a delivery system according to the invention.

Preferably, the delivery system incorporates the pH-reducing formulation of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

I. FORMULATION

1. Initial Studies

Lactide is readily hydrolyzed in water, even at room temperature. Hence, this material was tested for its pH neutralization ability.

An in vitro evaluation method was used, based on a procedure reported by Guthrie et al. (Industrial Engineering Chemistry, Vol. 44(9), pp 2187–88), according to which, the pH neutralization process of 4 ml of a 0.1 N NaOH solution, closely resembles that of a menstrual environment. The results of such a test, performed at room temperature using 75 mg of D,L-lactide to 4 ml of 0.1 N NaOH solution, are presented in Table 1.

TABLE 1

Reduction of the pH of 4 ml of 0.1N NaOH in the presence of 75 mg of lactide, as a function of time

| Time | pH |
|---|---|
| 0 | 12.45 |
| 5' | 4.30 |
| over night | 3.50 |

The highly effective nature of this substance in reducing the pH is obvious. Nevertheless, it was evident that in order to obtain a progressive pH decrease to <5.5 within ~0.5 hour and to maintain the pH at that level for approximately 4–6 hours (hereinafter "the prerequisite conditions"), a suitable formulation had to be produced. Therefore, both lactide and polylactic acid (PLA) were combined, the first causing immediate pH reduction and the latter, being hydrolyzed at a slower rate, resulting in prolonged pH reduction.

A combination of lactide (80%), D,L PLA—(Resomer-R-203, Boehringer, MW=30000) (10%) and poly (ethylene glycol) (PEG) MW-8000 (10%), was used and loaded onto a polymeric support in the form of weighed, rectangular shaped pieces of no non-woven (NW) tampon cloth (hereinafter: "strips") by evaporation from an acetone solution. PEG is a hydrosoluble compound which forms pores in the PLA matrix upon contact with water. The PEG molecules were added to the formulation in order to facilitate water penetration through the relatively hydrophobic PLA coating. The strips, mounted on microscope slides, were loaded with an approximate 50 mg net weight of lactide. The loaded strips were cut and tested in order to assess their pH neutralization efficacy. The tests were performed at room temperature and the results are presented in Table 2.

TABLE 2

Reduction of the pH of 4 ml of 0.1N NaOH in the presence of strips loaded with [LD 50 mg/D,L-PLA 30,000 5 mg/PEG 8000 5 mg], as a function of time

| Time | pH |
|---|---|
| 0 | 12.48 |
| 15' | 6.13 |
| 25' | 5.36 |
| 35' | 5.07 |
| 45' | 4.90 |
| 55' | 4.81 |
| 75' | 4.69 |
| 17 h | 4.33 |

This release profile is much more controlled than that of pure lactide powder.

A similar experiment was carried out in order to assess the pH neutralization efficacy of the samples in human plasma (Table 3).

TABLE 3

Reduction of the pH of 4 ml of plasma in the presence of NW loaded with [LD 50 mg/D,L-PLA 30,000 5 mg/PEG 8000 5 mg], as a function of time

| Time | pH |
|---|---|
| 0 | 7.43 |
| 1' | 6.60 |
| 5' | 6.08 |
| 10' | 5.80 |

TABLE 3-continued

Reduction of the pH of 4 ml of plasma in the presence of NW loaded with [LD 50 mg/D,L-PLA 30,000 5 mg/PEG 8000 5 mg], as a function of time

| Time | pH |
|---|---|
| 15' | 5.54 |
| 30' | 5.04 |
| 60' | 4.42 |
| 90' | 4.12 |
| 120' | 3.95 |

2. Method of Strip Preparation 2 ml of acetone solution containing a measured amount of the formulation were loaded on a strip (7.5×2.5 cm) by brushing and evaporation. The formulation-containing strips were folded 3 times around the axial direction and 7.5 cm-long strips were prepared by pressing the folded material at 1 ton/cm$^2$ for 30 seconds. 8 or 16 layered strips were obtained by using a single or double non-woven PP/PE respectively.

For all formulations, the preparation of 7.5 cm-long strips of either 8 or 16 layered (NW) cloth, proved to be most suitable for the gradual release of lactic acid. The release of lactic acid from all the formulations, or from a single or double layered cloth not in the form of a strip, was rapid and immediately decreased the pH of the NaOH solution. Such a behavior was not considered appropriate, taking into consideration the prerequisite conditions defined above. Hence, all formulations hereafter were designed and prepared as strips so as to attain the prerequisite conditions.

3. Formulation and in vitro Studies

Based on the results described above, a series of formulation and processing related studies were performed. Accordingly, two main aspects were investigated:

Formulation b. In vitro evaluation of formulated tampons

3a. Formulation Studies:

Among the different formulations studied, those which proved the most efficacious, are listed below and compared:

LD

LD/PEG 0.1 (=10% of weight of LD used)

LD/PLA 0.1

LD/PLA 0.1/PEG 0.1

All formulations were loaded on the strips by evaporation from an acetone solution applied to the strip, as described above.

In order to quantitatively evaluate the amount of lactide present in each formulated strip, a titration method was developed, as a quality control procedure, as follows:

The formulated strip is incubated in 80 ml of a 0.01N NaOH solution at 370° C. for 1 hour, a period during which the lactide is hydrolyzed to lactic acid. The solution is then titrated with 80 ml of a 0.01N HCl solution. Since 80 ml of 0.01N NaOH solution should be titrated by exactly 80 ml of 0.01N HCl solution, any difference in the titration amount (moles) of HCl, should account for an equivalent amount of lactic acid which was present in the sample.

3b. In vitro Studies

Figure 1:
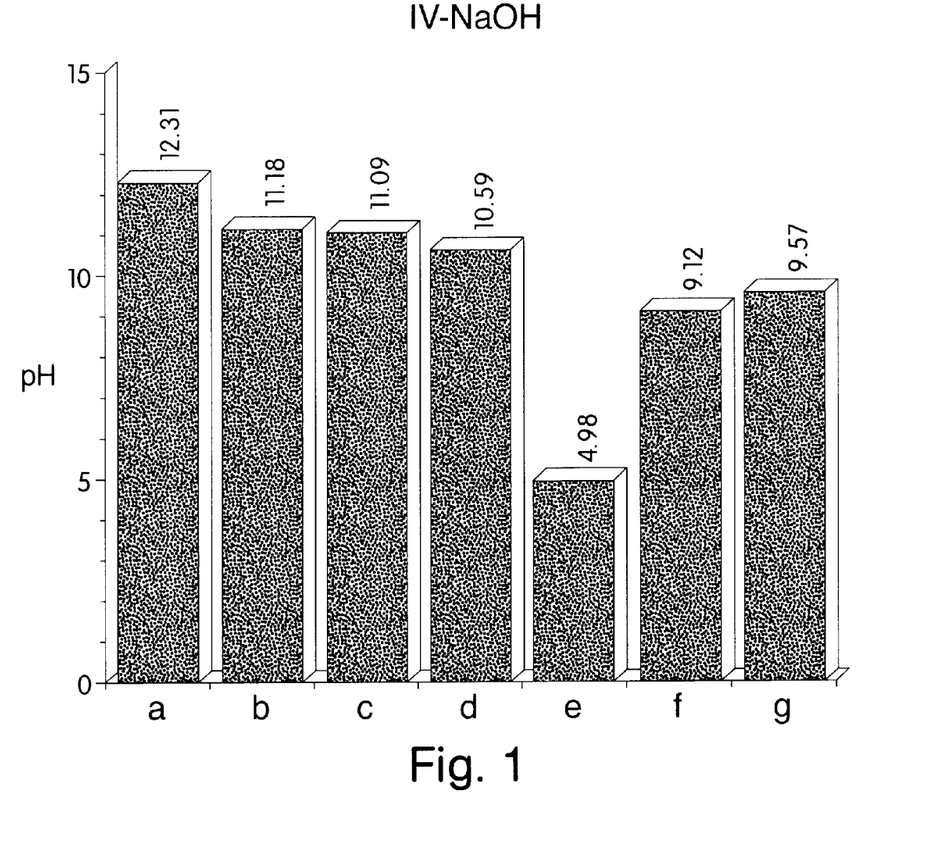
FIG. 1 shows the results of an in vitro study on the ability of various formulations to reduce the pH of 4 ml of 0.1 N NaOH: a. 0.1 N NaOH; b. water+0.1 N NaOH; c. water+0.1 N NaOH+untreated tampon; d. water+(tampon prewetted with 0.1 N NaOH); e. water+0.1 N NaOH+strip containing formulation; f. tampon with 2 strips containing formulation inserted bilaterally lengthwise (T/L); g. tampon with 2 strips containing formulation inserted bilaterally widthwise (T/W)
Figure 2:
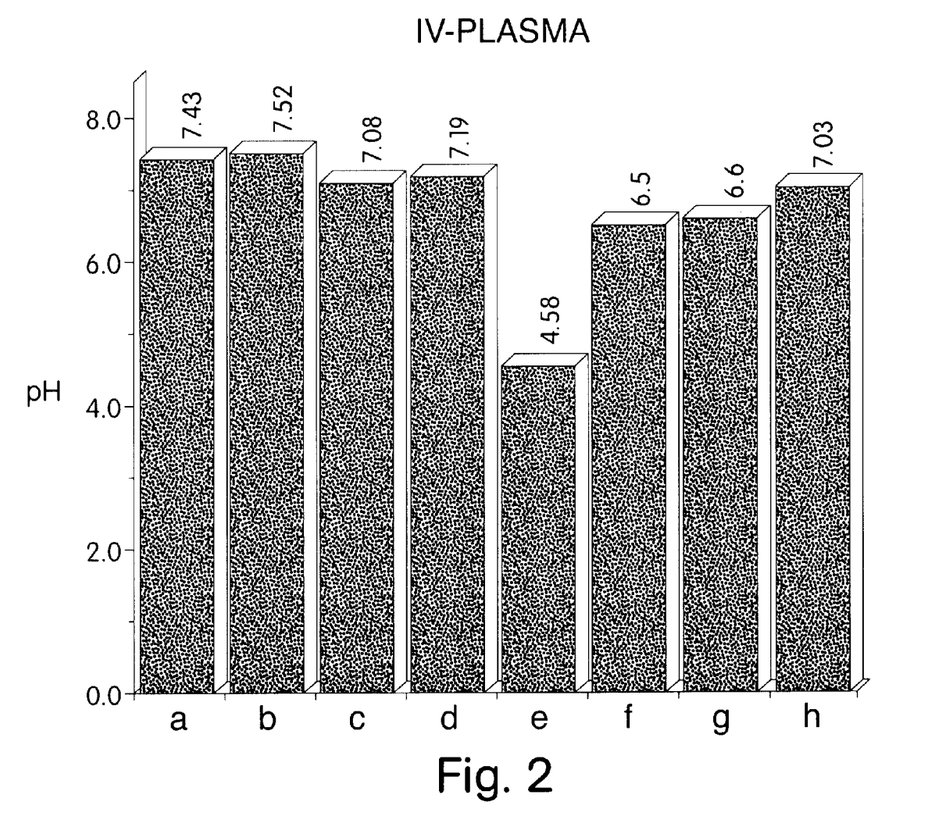
FIG. 2 shows the results of an in vitro study on the ability of various substances to reduce the pH of 4 ml of plasma; a. plasma; b. water+plasma; c. water+plasma+untreated tampon; d. water+(tampon prewetted with plasma); e. water+plasma+strip containing formulation; f. T/L; g. T/W; h. rolled-type tampon with 2 strips containing formulation inserted bilaterally lengthwise (T/D)

Folded and pressed tampons (folded-type tampons—see Examples 1 and 2 below) were used in the majority of the following studies. The formulated strip-containing tampons (strips were introduced as described in FIGS. 8 and 9 below) were tested in vitro with a 4 ml 0.1N NaOH solution or with plasma, both subsequently diluted in 75 ml of ×2 distilled water, for measurement purposes. Either plasma or the 0.1N NaOH solution was dripped at a 0.1 ml/min rate at 37° C. and incubated for another 20 min (1 hour in total) before dilution and measurement. The results are summarized in FIGS. 1 and 2. It can be seen from these figures that the strip containing the formulation was the most effective in reducing the pH.

4. Improving Lactic Acid (LA) Release from Strip-Containing Tampon

The distinct difference in behavior between the formulated strip without a tampon and the strip-containing tampon is reflected in the resulting final pH values obtained in the in vitro studies described above.

The distinct decrease in LA release of the strip-containing tampon in comparison to that the strip itself was related to the fact that not the whole length of the strip is wetted by the 4 ml volume of the added liquid, the strips being positioned lengthwise bilaterally underneath the outer layer of the tampon (see chapter on delivery system, below). According to the wetting profile obtained by using 4 ml of water containing methylene blue (not shown), only about a third of the strip's length was wetted.

According to these results, the total amount of formulated lactide was increased 3 and 6 fold per tampon in order to ensure the eventual release of the appropriate amount of lactic acid able to reduce the pH to the desired value in the tampon and/or in the surroundings. Increasing the amount of lactide was not expected to have an adverse effect, or to markedly reduce the pH below 3.

All in vitro studies hereafter were carried out in a device (named "SYNCTNA"), recommended by the US FDA to simulate the lateral pressure acting on the tampon under natural conditions. Thus, the wetting profile inside the tampon would resemble the natural conditions as closely as possible. Plasma, heated to 37° C., was added dropwise to the tampon inside the SYNGINA for a period of 20 min., after which the tampon was kept at 37° C. for an additional 40 minutes (60 min. in total) The tampon was then immersed in 75 ml of ×2 distilled water, thoroughly squeezed for several seconds at which stage the pH was measured.

Figure 3:
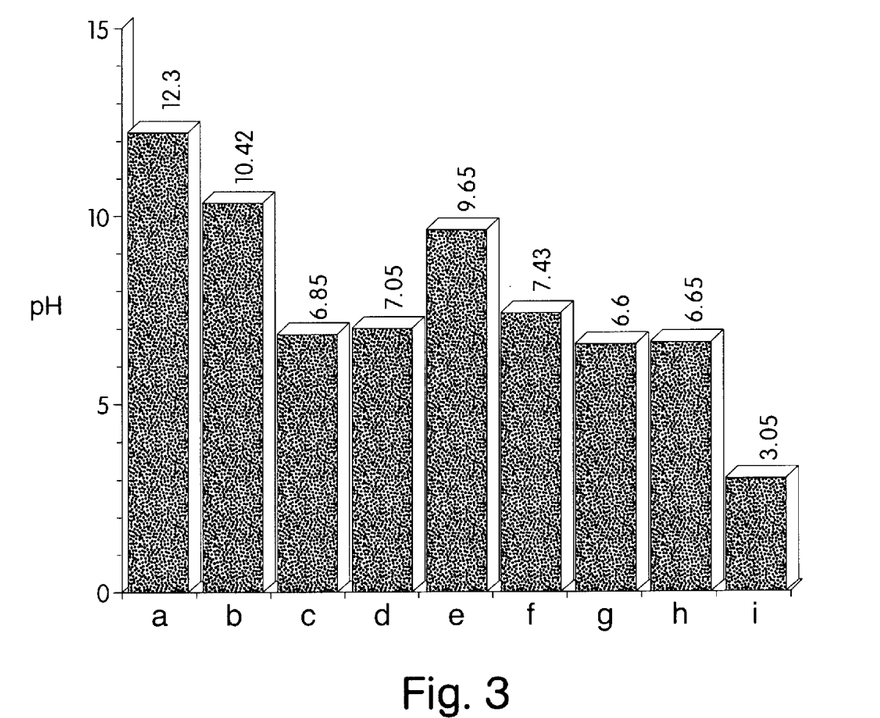
FIG. 3 shows the results of a SYNGINA study of tampons containing 3 strips with ×1, ×3 and ×6 the original amount of formulated lactide: a. 4 ml of 0.1 N NaOH+75 ml water; b. Playtex™ tampon; e. T/L 3 strips containing together ×6 the original amount of formulation (3×6); d. T/L (3×3); e. T/D (1×1); f. plasma (PL); g. T/L-PL (3×6); h. T/L-PL (3×3); i. strips without tampon (3×3)

FIG. 3 illustrates the final pH obtained in both plasma (PL) and the 0.1N NaOH solution, with ×1, ×3 and ×6 the original amount of the formulation [LD 80%/D,L-PLA2000 10%/PEG8000 10%], equally divided between 3 strips per tampon. In the NaOH 0.1N solution, the ×3 concentration lowers the pH significantly more than ×1. Nevertheless, pH 7 is much higher than the desired pH 5.5. Also, no further decrease in pH is achieved by doubling the amount to ×6. The ×3 strip itself however, efficiently lowered the pH. This led to the conclusion that the amount of formulated substance is not the only parameter affecting LA release. All the formulations hereafter contained ×3 amounts.

The second parameter which may affect LA release from the strip-containing tampon, stems from the possibility that the tampon material is more wettable than the strip itself, thus diminishing the accessibility of the liquid to the strip.

To overcome this effect, different formulations, of increased hydrophilicity were tested. Also, 8 and 4 layered laterally welded strips, positioned centrally in the tampon were used instead of the two 16 layered pressed strips used initially. The hydrophilisation process was achieved by either increasing the PEG content or by replacing it with the more hydrophilic substance, glycerol.

Figure 4A:
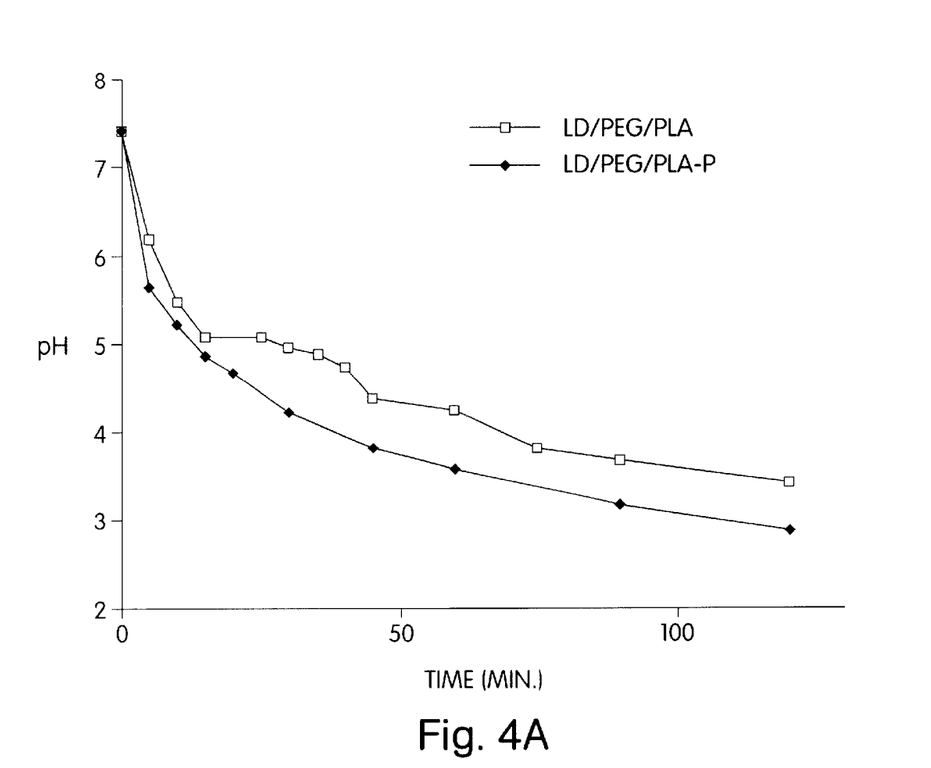
FIGS. 4a & 4b are graphs showing lactic acid release kinetics from welded or pressed (P) strips containing various formulations, by following pH decrease in plasma.
Figure 4B:
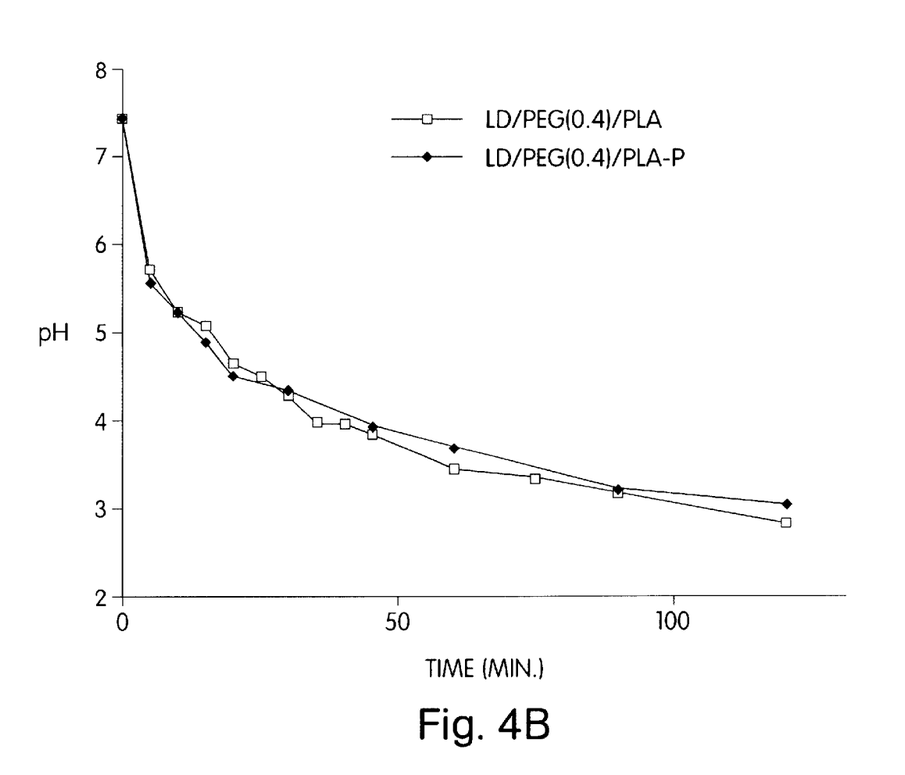

First, the effect of both formulation and processing on the release kinetics of the strips themselves was tested. The graphs in FIGS. 4A and 4B illustrate representative results.

In strips, all formulations seemed to perform similarly well, with a distinct difference between pressed and welded samples. In contrast to the expected effect, in most cases the pressed strips exhibited a more accelerated release pattern than the welded ones. A reasonable explanation for this behavior is the possible formation of embedded LD in polymeric matrix caused by the local strip PE melting process. This effect, however, was not observed in the most hydrophilic formulations.

5. Effect of Strip Positioning

The most favorable strip positioning proved to be the use of a plurality of strips, preferably two strips and most preferably three strips positioned on opposite sides of the tampon, so that the strips are closer to the tampon surface at the end of the manufacturing process. Positioning the SYNGINA containing the tampon at 45° did not significantly effect the results.

6. Citric Acid-Containing Formulations

Most of the possible parameters influencing efficacy of pH adjustment were explored. At this stage, an in vitro pH value lower than 5.5–5.7 was very difficult to achieve. It was concluded that the active ingredient itself, i.e. lactide, is probably the limiting factor in this case. Although, as described in the initial study section, lactide is the PLA of the lowest possible molecular weight, it is still hydrophobic and is dissolved in water (and thus released as lactic acid) only after hydrolysis. It was thus decided that an additional organic acid should be included in the formulation. Citric acid (CA) proved to be the most suitable candidate, being both hydrophilic and crystalline as well as constituting a natural metabolite in the human body, as lactic acid.

Including CA in the formulation would, in parallel, contribute to:

shortening response induction time to an actual instant response; the lactide component contributing to a longer term response;

lowering formulation costs, by decreasing the necessary amount of lactide—CA being of a significantly lower price than lactide.

Figure 5:
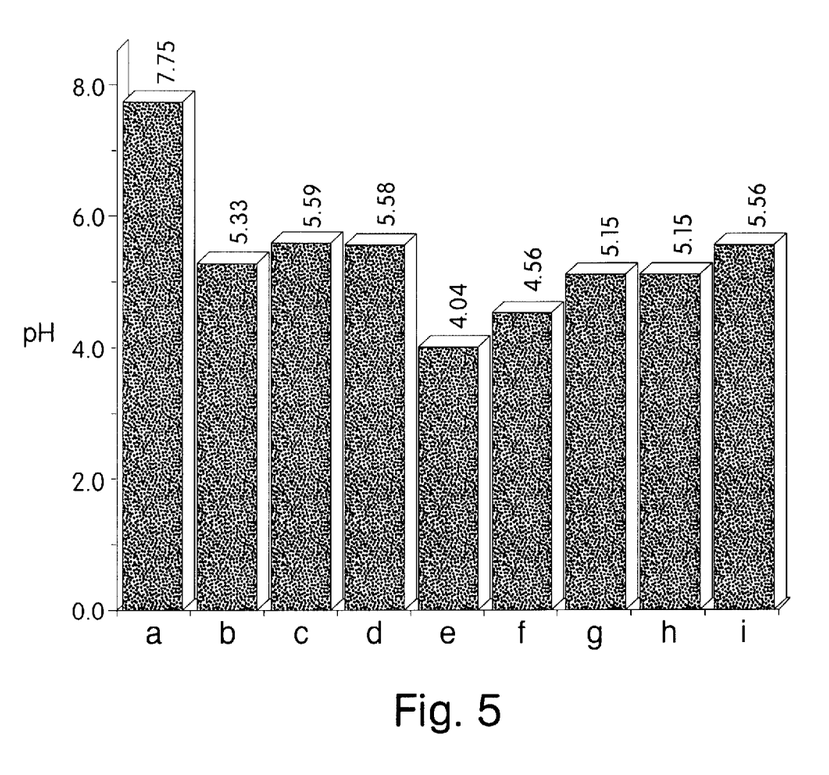
FIG. 5 shows the results of a SYNGINA study of tampons having citric acid-containing strips prepared by immersion; a. plasma; b. Lactide (LD) 100 mg/glycerol (Glyc) 15%/Tween 80 (TW) 5% (I); c. LD 100 mg/Glyc 15%/TW 5% (II); d. F-17; e. LD 100 mg/Glyc 15%/TW 5% C-20 mg; f. LD 50 mg/Glyc 15%/TW 5% C-20 mg; g. LD 25 mg/Glyc 15% C-20 mg; h. LD 25 mg/Glyc 15% C-15 mg; i. C-20 mg/Glyc 15%.
Figure 6A:
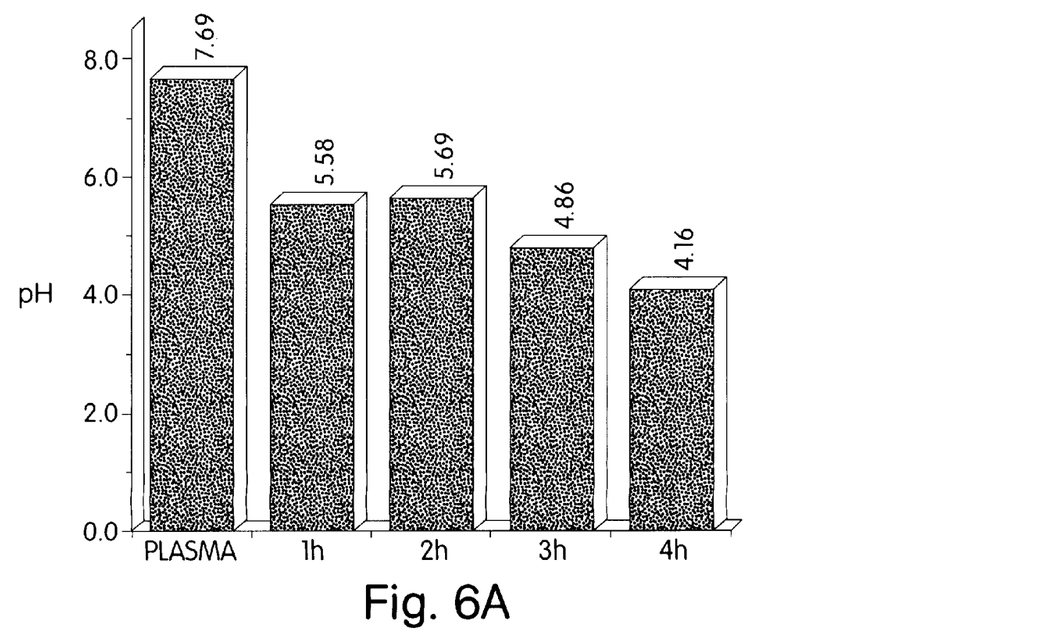
FIGS. 6a–6d show the results of a SYNGINA time-response study of tampons having citric acid-containing strips prepared by immersion; a. LD-L 100 mg; b. LD 100 mg/citric acid (CA) 20 mg; c. LD 50 mg/CA 20 mg; d. LD 25 mg/CA 20 mg.
Figure 6B:
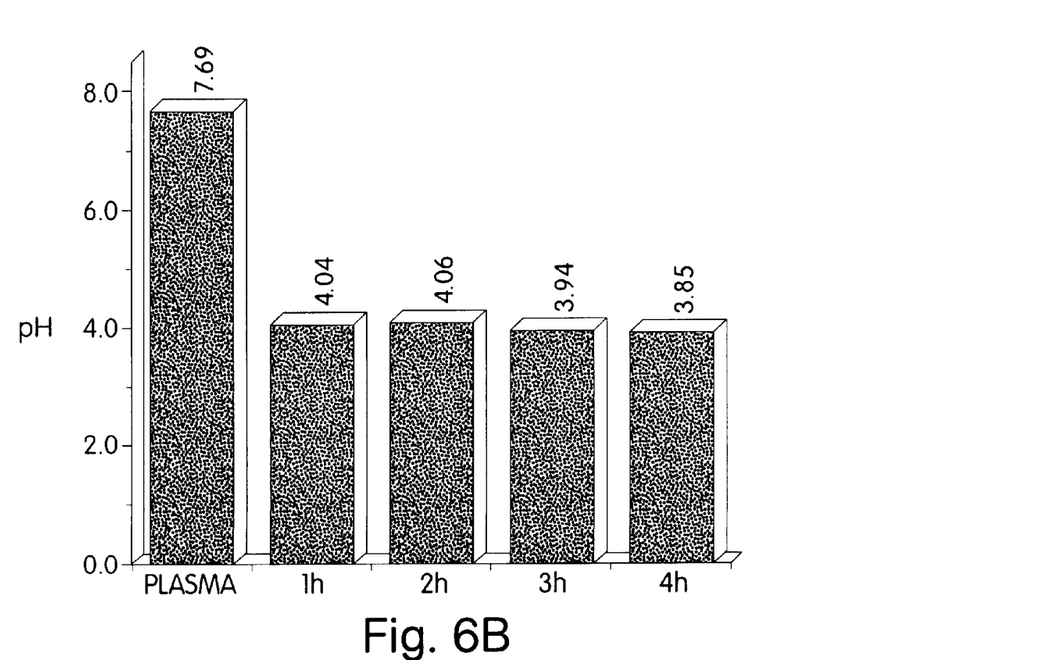
Figure 6C:
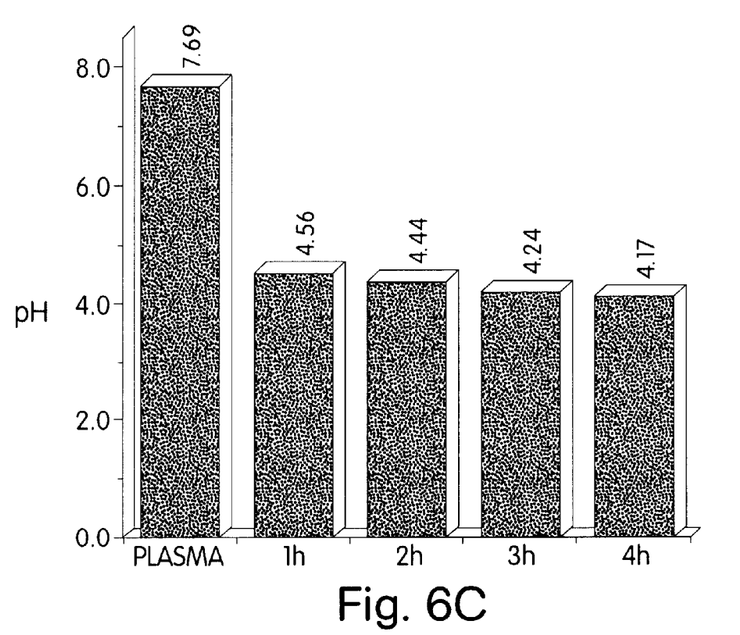
Figure 6D:
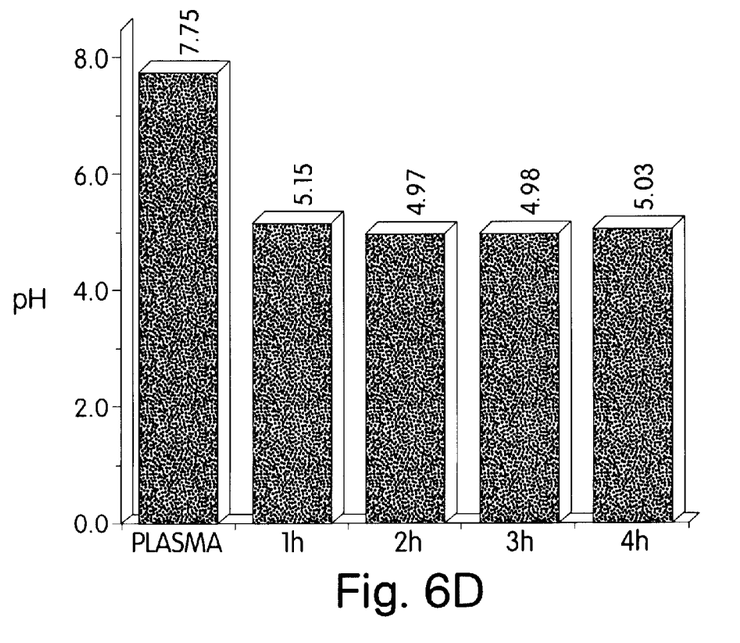

First, 4 ml of plasma were titrated with CA in order to assess the required amount of CA in the formulation. Even though the buffering effect of the plasma is evident, only 22.8 mg of CA were necessary to lower the pH to 5. Accordingly, 20 mg of CA were used in formulations containing decreasing amounts of lactide in combination with glycerol with or without tween 80 (FIG. 5).

The optimal formulation among those tested, was the one containing 50 mg lactide, 20 mg CA, 7.5 mg glycerol and 2.5 mg Tween-80 (named C-2). PEG may be used to replace Tween In addition, a time response study was performed on four of the formulated tampons exhibited in FIG. 5. Again, C-2 proved to be the optimal formulation (FIGS. 6a–d), initially lowering the pH to 4.56 within the first hour, and further decreasing it to 4.17 by the end of a four-hour incubation period.

Figure 7:
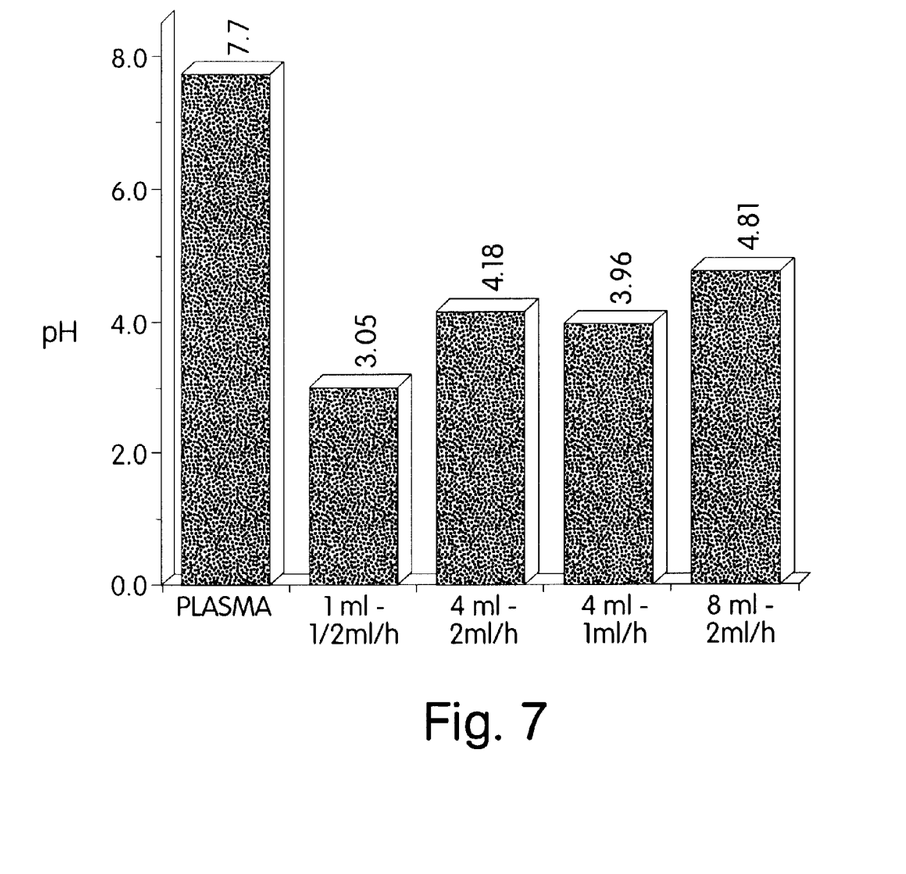
FIG. 7 shows the results of a SYNGINA time-response study of tampons having citric acid-containing strips incubated at 37° C.

Finally, a formulation, C-2B, similar to C-2 only without the Tween 80, was tested in the SYNGINA in a 37° C. room by dripping different plasma volumes for different time periods, at 5 min intervals. The results are presented in FIG. 7. Although under these conditions the response appeared to be somewhat faster, a similar final pH value of about 4 was obtained. With plasma amounts lower than 4 ml, pH values were significantly lower, the extraction method used in these studies being unsuitable in this case. With 8 ml of plasma, an expected higher pH value of 4.8 was measured.

II. Delivery System

The delivery system of the invention is composed of a polymeric support, such as a non-woven polymer, on which a deposition is deposited. The deposition comprises an active agent which may be released to the surrounding environment. Examples of such active agents include bactericidal agents, deoderizing agents, medically active substances and pH controlling agents. In a preferred embodiment, the pH controlling agent is the formulation disclosed above. In one embodiment, the active agent is dissolved in a solvent which is applied to the support. The deposition is deposited by evaporation of the solvent The polymeric support is placed near the surface of the tampon. Preferably, the delivery system is positioned between the inner absorbent core of the tampon and its outer covering layer. The polymeric support may be in any geometrical form or shape. Preferably, the support is in the form of rectangular strips of material, although other shapes are also possible. A plurality of these strips may be placed on different sides of the tampon in order to release the active agent in all directions. In the following discussion, several non-limiting examples are provided of tampons prepared according to the invention.

EXAMPLE 1

Tampons which undergo both radial and longitudinal expansion are generally manufactured for use with various types of applicator devices. The longitudinal expansion is generally more than 10% of its unexpanded length. This type of tampon comprises an inner core of absorbent material, such as cellulose fibers and/or cotton fibers, enveloped by an outer layer of liquid permeable material such as a non-woven polymer, as for example polypropylene, polyethylene, polyester, cellulose, cellulose derivatives, or any combination of the above. This type of tampon is referred to in this specification as a "folded-type" tampon.

Figure 8A:
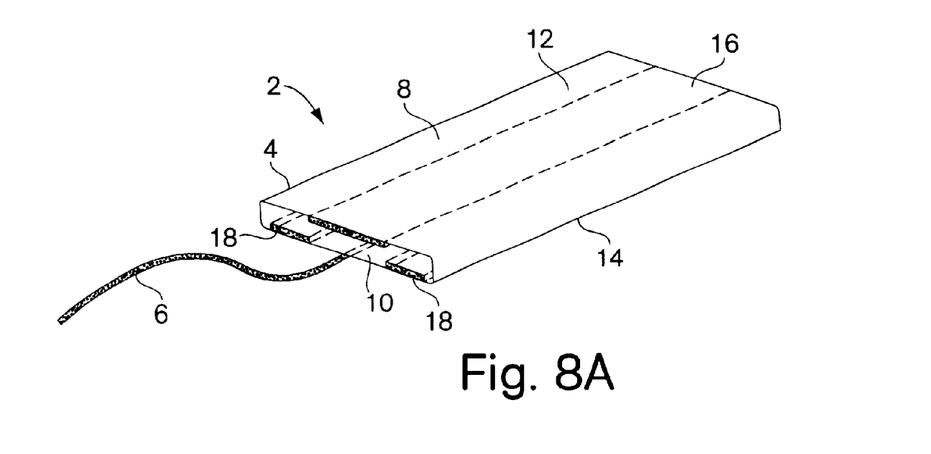
FIGS. 8a and 9a are perspective top views of a folded-type tampon in its flat form with two different embodiments of a delivery system in accordance with the invention.

A folded-type tampon according to one embodiment of the invention is illustrated in FIG. 8a, in which can be seen a tampon 2 in its flat form comprising a body 4 and withdrawal cord 6. The body 4 of the tampon comprises an outer layer 8 enveloping an inner absorbent core 10. The outer layer is held to the inner core in ways well known in the art, such as sewing or welding. The flat body has an upper 12 end a lower 14 surface.

In this embodiment, a delivery system according to the invention in the form of three rectangular polymeric strips are positioned between the outer layer and the inner core, in parallel to the longitudinal axis of the body. One relatively wide strip 16 is on the upper surface 12 of the body (under the outer layer 8) and two narrow strips 18 are on the lower surface 14. The length of the strips may be approximately equal to the length of the flat body, and preferably equal to it. Preferably, the width of the wide strip is approximately twice the width of the narrow strips. Typical, non-limiting dimensions may be as follows: length and width of flat tampon—5–9.5 and 4–5 cm, respectively; widths of wide and narrow strips—1.5–2.5 cm and 0.7–1.5 cm, respectively.

Figure 8B:
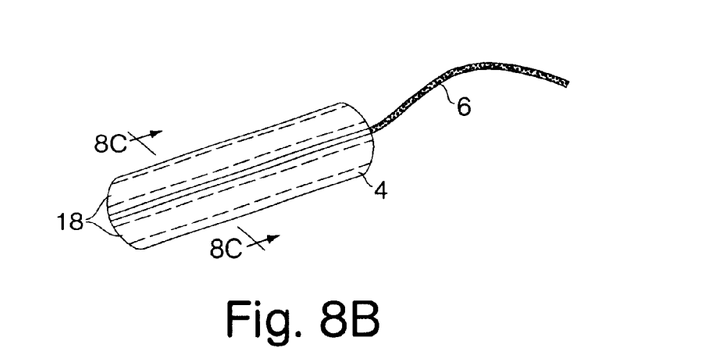
FIGS. 8b and 9b are perspective views of a folded-type tampon in its final folded and pressed form.
Figure 8C:
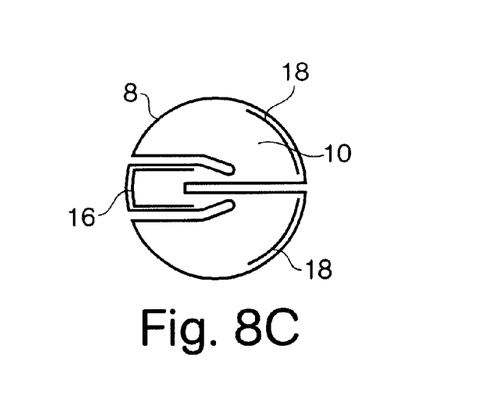
FIGS. 8c and 9c are sectional views along lines 8c—8c and 9c—9c in FIGS. 8b and 9b, respectively.

When the tampon is folded, it is compressed both lengthwise and widthwise to form the conventional tampon shape, as shown in FIG. 8b. The strips 18 are aligned near the outer surface of the body of the tampon. The tampon takes on a W-like shape in cross-section, as illustrated in FIG. 8c, in which can be seen the inner core 10, the outer layer 8 and the wide 16 and narrow 18 strips below the outer layer. It may be seen from the figure that the edges of the wide strip 16 are folded within the folds of the inner core 10, thereby releasing the active agent absorbed therein to within the tampon as well as to the surrounding environment.

EXAMPLE 2

Figure 9A:
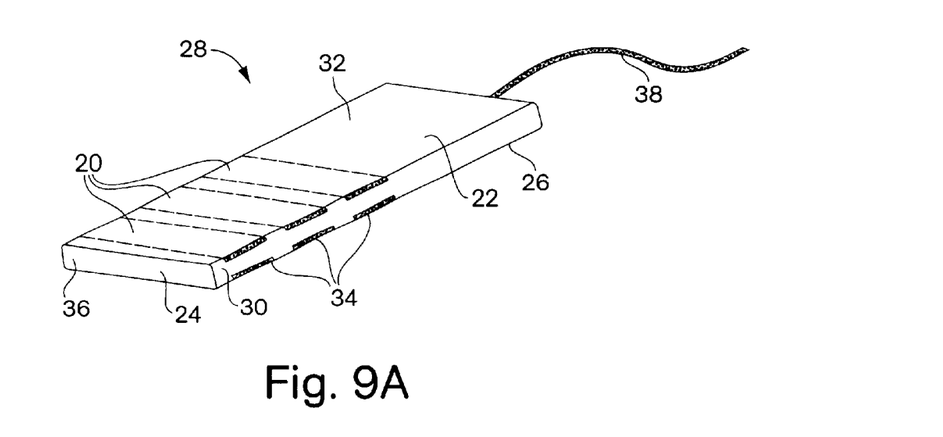

In another embodiment, illustrated in FIG. 9a, three strips are positioned at spaced intervals between the outer layer 22 and the inner core 24 of the flat tampon 28, perpendicularly to the longitudinal axis of the flat body 26 of the tampon. In this embodiment, the strips are wound around the width of the body 26 and then excised at the: lateral edges 30 of the body so that there are 3 strips 20 on the upper surface 32 of the body and 3 corresponding strips 34 on the underside of the body. The length of each of the strips is equal to the width of the flat tampon. Preferably, the strips are positioned closer to the front end 36 of the tampon, opposite the withdrawal cord 38, since this is the end with which the menstrual fluid first comes into contact.

Figure 9B:
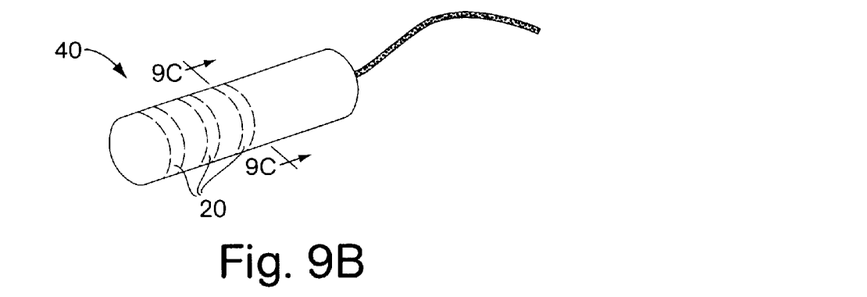
Figure 9C:
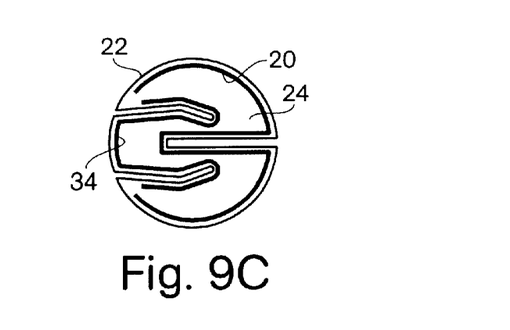

The folded tampon 40 is illustrated in FIG. 9b, in which can be seen the annular strip 20. FIG. 9c shows how the strips 20,34 appear near the outer surface of the tampon between the outer layer 22 and the inner core 24, as well as within the folds of the inner core.

EXAMPLE 3

Figure 10A:
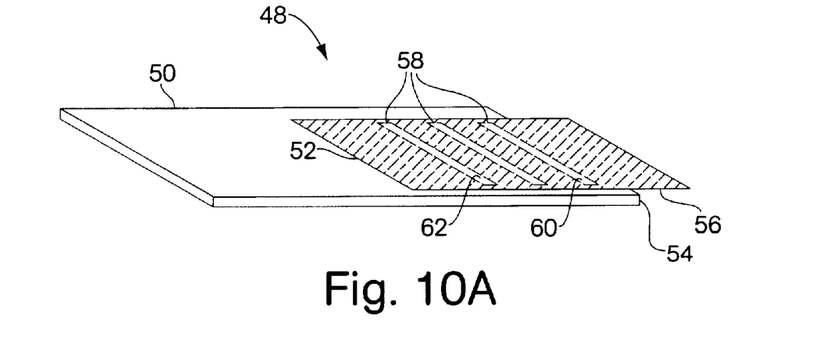
FIGS. 10a and 11a are perspective top views of a rolled-type tampon in its flat form with two different embodiments of a delivery system in accordance with the invention.
Figure 10B:
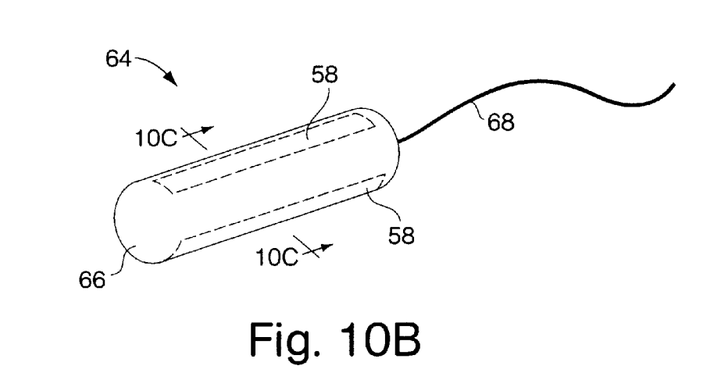
FIGS. 10b and 11b are perspective views of a rolled-type tampon in its final, rolled and pressed form.
Figure 10C:
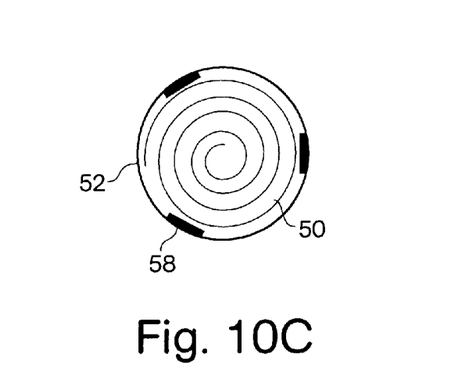
FIGS. 10c and 11c are sectional vies along lines 10c—10c and 11c—11c in FIGS. 10b and 11b, respectively.

A typical tampon which undergoes primarily radial expansion (<10% longitudinal expansion, if at all) is referred to in this specification as a "rolled-type" tampon and is shown in FIGS. 10a–10c. As in the folded-type tampon described above, it comprises an inner core of absorbent material, as in Example 1, enveloped by an outer layer of liquid permeable material, as in Example 1. The rolled-type tampon differs from the folded-type tampon, inter alia, in their dimensions as well as in the manner of forming of the tampon. These differences affect the placement of the strips.

As shown in FIG. 10a, the flat tampon 48 comprises an absorbent layer 50 on which is placed an outer layer 52. The absorbent layer 50 is in the form of an extended rectangular ribbon. The material of the outer layer 52 is generally heat sealed to the upper side of the absorbent layer near one of its ends 54, an extension 56 of the outs layer partly extending beyond the end 54 of the absorbent layer. The length of the extension 56 is substantially equivalent to the circumference of the tampon in its final, folded form.

According to one embodiment of the invention, three parallel spaced rectangular polymeric strips 58 are positioned equidistantly from each other, perpendicular to the longitudinal axis of the outer layer, and between the absorbent layer 50 and the outer layer 52. The ends of the strips are distanced from the longitudinal edges of the outer layer, and the strip 60 closest the end 54 of the absorbent layer is inwardly displaced from that end. The distance from the strip 62 farthest from the end 54 of the absorbent layer to that end is approximately equal to the circumference of the tampon in its folded form.

Typical, non-limiting dimensions of the various tampon components are given below for exemplary purposes only: length, width and thickness of absorbent layer—20–30 cm, 4–6 cm and 0.4–1.0 cm, respectively; length and width of outer layer—5–15 cm and 4–4.5 cm; circumference of tampon—3–4.5 cm; length of strips—3.5–5.5 cm.

FIG. 10b shows the tampon 64 in its folded form comprising the body 66 and withdrawal cord 68. During the forming process, the absorbent layer of the flat tampon (FIG. 10a) is rolled up onto itself along its longitudinal axis towards the end on which the strips and outer layer are placed, and the extension 56 of the outer layer is heat welded to the opposite end of the outer layer, thus enveloping the absorbent layer which now forms the core of the tampon. Two of the three strips 58 may be seen in FIG. 10b through the outer layer, with the third strip out of sight behind the body of the tampon. FIG. 10c shows the three components of the tampon according to the invention: the rolled up inner absorbent core 50, the outer layer 52 and the strips 58.

EXAMPLE 4

Figure 11A:
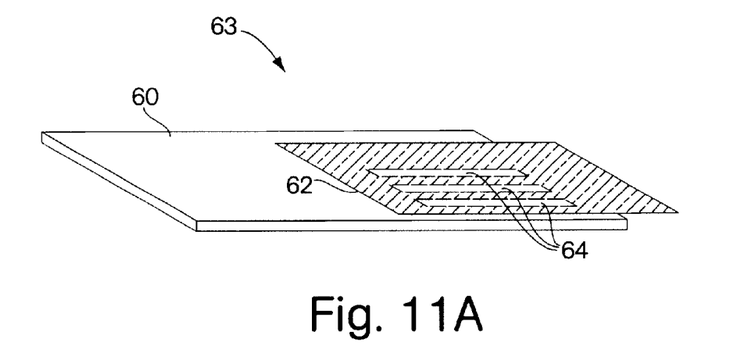
Figure 11B:
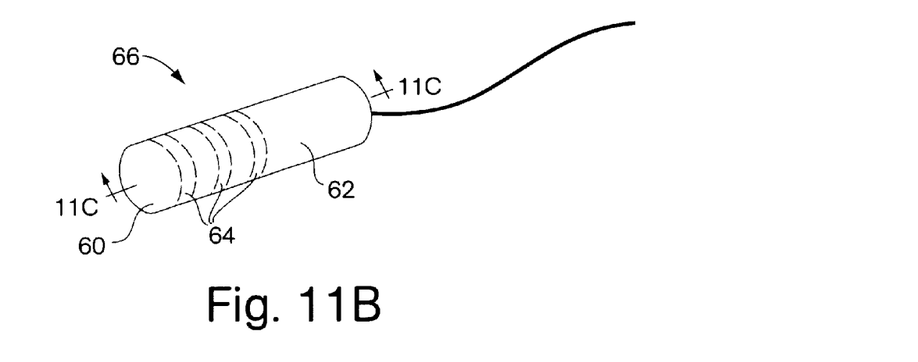
Figure 11C:
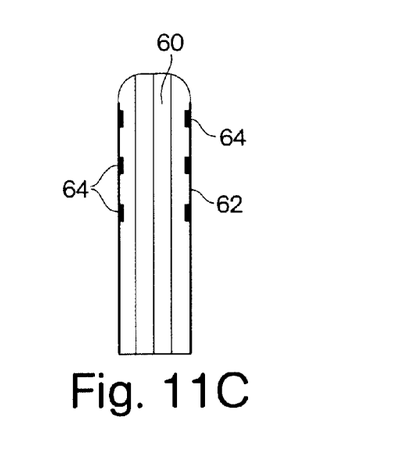

In this embodiment, illustrated in FIGS. 11a–11c, the strips are placed parallel to the longitudinal axis of the outer layer rather than perpendicular thereto. Thus, FIG. 11a illustrates the absorbent layer 60 and outer layer 62 of the flat tampon 63 as in the previous example. Three parallel equidistant strips 64 are placed between the two layers in parallel to the longitudinal axis of the outer layer. The length of each strip is equal to the circumference of the tampon in its final form. Preferably, the strips are placed proximate to the anterior end of the folded tampon.

FIGS. 11b and 11c show the tampon 66 in its folded form comprising the inner core 60, the outer layer 62 and the strips 64.

What is claimed is:

1. A formulation effective in reducing the pH in a menstruating vagina or in a tampon inserted therein to below pH 5.5 comprising:
   (a) 3–80% by weight of lactide;
   (b) 92–15% by weight of a solid organic acid; and
   (c) 5–30% of a wetting agent.

2. A formulation effective in reducing the pH in a menstruating vagina or in a tampon inserted therein to below pH 5.5 comprising:
   (a) 3–80% by weight of polylactic acid in the range of from approximately 200–2000 MW;
   (b) 92–15% by weight of a solid organic acid; and
   (c) 5–30% of a wetting agent.

3. A formulation according to claim 1 wherein said lactide is DL-lactide or L-lactide.

4. A formulation according to claim 1 wherein said solid organic acid is selected from the group consisting of citric, malic, maleic, fumaric, succinic, tartaric and oxalic acids.

5. A formulation according to claim 1 wherein said wetting agent is selected from the group consisting of glycerol, polyethylene glycol (PEG), polypropylene glycol (PPG) and surfactants with an HLB ranging from 10 to 18.

6. A delivery system for releasing an active agent within the female urogenital tract, comprising:
   (a) a female hygienic product comprising an inner absorbent core, an outer covering layer and at least one polymeric support comprising one or more layers and positioned between said inner absorbent core and said outer covering layer; and
   (b) a deposition covering at least a part of said polymeric support, the deposition comprising said active agent, the deposition comprising 3–80% by weight of lactide, 92–15% by weight of a solid organic acid; and 5–30% of a wetting agent.

7. A delivery system according to claim 6 wherein said polymeric support comprises three separate strips.

8. A delivery system according to claim 6 wherein the components of said deposition are dissolved in a solvent and the deposition is deposited by evaporation of said solvent.

9. A delivery system according to claim 6 wherein said polymeric support comprises a non woven polymer.

10. A delivery system according to claim 6 wherein said polymeric support is in the form of a strip.

11. A delivery system according to claim 10 wherein said strip consists of a plurality of layers.

12. A delivery system according to claim 11 wherein said strip consists of 2–16 layers.

13. A tampon for insertion in a human vagina comprising:
   (a) an inner absorbent core, an outer covering layer and at least one polymeric support comprising one or more layers and positioned between said inner absorbent core and said outer covering layer; and
   (b) a deposition covering at least a part of said polymeric support, the deposition comprising said active agent, the deposition comprising 3–80% by weight of lactide, 92–15% by weight of a solid organic acid; and 5–30% of a wetting agent.

14. A tampon according to claim 13 wherein said delivery system comprises a plurality of strips of the polymeric support.

15. A tampon according to claim 13 wherein said polymeric support comprises three separate strips.

16. A tampon comprising a formulation effective in reducing the pH in the vagina of a menstruating woman comprising:
   (a) 3–80% by weight of polylactic acid in the range of from approximately 200–2000 MW;
   (b) 92–15% by weight of an organic acid; and
   (c) 5–30% of a wetting agent.

17. A tampon according to claim 13 or 16 wherein said solid organic acid is selected from the group consisting of citric, malic, maleic, fumaric, succinic, tartaric and oxalic acids.

18. A tampon according to claim 13 or 16 wherein said wetting agent is selected from the group consisting of glycerol, polyethylene glycol (PEG), polypropylene glycol (PPG) and surfactants with an HLB ranging from 10 to 18.

19. A formulation according to claim 1 further comprising an anti-inflammatory agent.

20. A delivery system according to claim 7 further comprising an anti-inflammatory agent.

21. A tampon according to claim 13 or 16 further comprising an anti-inflammatory agent.

22. A delivery system according to claim 6 wherein said lactide is DL-lactide or L-lactide.

23. A tampon according to claim 13 wherein said lactide is DL-lactide or L-lactide.

* * * * *